US00PP24970P2

(12) United States Plant Patent
van Noort

(10) Patent No.: US PP24,970 P2
(45) Date of Patent: Oct. 14, 2014

(54) ***SEDUM* PLANT NAMED 'CHOCOLATE CHERRY'**

(50) Latin Name: *Sedum telephium*
Varietal Denomination: Chocolate Cherry

(71) Applicant: Marco van Noort, Warmond (NL)

(72) Inventor: Marco van Noort, Warmond (NL)

(73) Assignee: Marco van Noort Breeding B.V., Warmond (NL)

( * ) Notice: Subject to any disclaimer, the term of this patent is extended or adjusted under 35 U.S.C. 154(b) by 0 days.

(21) Appl. No.: 13/694,218

(22) Filed: Nov. 7, 2012

(51) Int. Cl.
*A01H 5/00* (2006.01)

(52) U.S. Cl.
USPC ..... Plt./479

(58) Field of Classification Search
CPC ..... A01H 5/00
USPC ..... Plt./479
See application file for complete search history.

*Primary Examiner* — Susan McCormick Ewoldt
(74) *Attorney, Agent, or Firm* — C. A. Whealy

(57) ABSTRACT

A new and distinct cultivar of *Sedum* plant named 'Chocolate Cherry', characterized by its broadly upright plant habit; basally branching habit; glossy dark greyed purple-colored leaves; numerous light red purple-colored flowers; good garden performance.

3 Drawing Sheets

Botanical designation: *Sedum telephium.*
Cultivar denomination: 'CHOCOLATE CHERRY'.

BACKGROUND OF THE INVENTION

The present invention relates to a new and distinct cultivar of *Sedum* plant, botanically known as *Sedum telephium* and hereinafter referred to by the name 'Chocolate Cherry'.

The new *Sedum* plant is a product of a planned breeding program conducted by the Inventor in Warmond, The Netherlands. The objective of the breeding program is to create new strong, healthy and freely-flowering *Sedum* plants with attractive leaves and flowers.

The new *Sedum* plant originated from an open-pollination in July, 2010 in an outdoor nursery Warmond, The Netherlands of *Sedum telephium* 'Karfunkelstein', not patented, as the female, or seed, parent with an unknown selection of *Sedum telephium*, not patented, as the male, or pollen, parent. The new *Sedum* plant was discovered and selected by the Inventor as a single flowering plant within the progeny of the stated open-pollination in an outdoor nursery in August, 2011.

Asexual reproduction of the new *Sedum* plant by cuttings and by divisions in a controlled environment in Warmond, The Netherlands since March, 2012 has shown that the unique features of this new *Sedum* plant are stable and reproduced true to type in successive generations.

SUMMARY OF THE INVENTION

Plants of the new *Sedum* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Chocolate Cherry'. These characteristics in combination distinguish 'Chocolate Cherry' as a new and distinct *Sedum* plant:

1. Broadly upright plant habit.
2. Basally branching habit.
3. Glossy dark greyed purple-colored leaves.
4. Numerous light red purple-colored flowers.
5. Good garden performance.

Plants of the new *Sedum* differ from plants of the female parent, 'Karfunkelstein', primarily in flower bud and flower color as plants of 'Karfunkelstein' have dark green-colored flower buds and pinkish purple-colored flowers.

Plants of the new *Sedum* can also be compared to plants of *Sedum telephium* 'Purple Emperor', not patented. Plants of the new *Sedum* and 'Purple Emperor' differ primarily in leaf and flower color as plants of 'Purple Emperor' have greenish purple-colored leaves and pink-colored flowers.

BRIEF DESCRIPTION OF THE PHOTOGRAPHS

The accompanying colored photographs illustrate the overall appearance of the new *Sedum* plant showing the colors as true as it is reasonably possible to obtain in colored reproductions of this type. Colors in the photographs may differ slightly from the color values cited in the detailed botanical description which accurately describe the colors of the new *Sedum* plant.

The photograph on the first sheet comprises a side perspective view of a typical flowering plant of 'Chocolate Cherry' grown in a container.

The photograph on the second sheet is a close-up view of typical inflorescences of 'Chocolate Cherry'.

The photograph on the third sheet is a close-up view of a typical leaf of 'Chocolate Cherry'.

DETAILED BOTANICAL DESCRIPTION

The aforementioned photographs and following observations, measurements and values describe plants grown during the late summer and early autumn in an outdoor nursery in Warmond, The Netherlands and under cultural practices typical of commercial *Sedum* production. During the production of the plants, day temperatures ranged from 12° C. to 32° C.

and night temperatures ranged from 6° C. to 18° C. Plants were two years old when the photographs and description were taken. In the following description, color references are made to The Royal Horticultural Society Colour Chart, 2007 Edition, except where general terms of ordinary dictionary significance are used.

Botanical classification: *Sedum telephium* 'Chocolate Cherry'.

Parentage:

*Female, or seed, parent.*—*Sedum telephium* 'Karfunkelstein', not patented.

*Male, or pollen, parent.*—Unknown selection of *Sedum telephium*, not patented.

Propagation:

*Type.*—By cuttings.

*Time to initiate roots, summer.*—About 14 days at temperatures ranging from 16° C. to 20° C.

*Time to produce a rooted young plant, summer.*—About 12 to 18 days at temperatures ranging from 16° C. to 20° C.

*Root description.*—Thick, fleshy; creamy yellow to brown in color.

*Rooting habit.*—Low branching; sparse.

Plant description:

*Plant form/habit.*—Herbaceous perennial; broadly upright plant habit; moderately vigorous growth habit; freely basally branching habit with about 27 lateral branches developing per plant.

*Plant height.*—About 35 cm.

*Plant width (spread).*—About 48.1 cm.

*Lateral branches.*—Length: About 18.3 cm. Diameter: About 7 mm. Internode length: About 4.4 cm. Strength: Strong. Texture: Smooth, glabrous. Color: Close to 187B.

Foliage description:

*Arrangement.*—Opposite, simple; sessile.

*Length.*—About 5.4 cm.

*Width.*—About 3.2 cm.

*Shape.*—Ovate, slightly carinate.

*Apex.*—Bluntly acute.

*Base.*—Cordate.

*Margin.*—Irregularly and shallowly dentate.

*Texture, upper and lower surfaces.*—Smooth, glabrous; succulent.

*Luster, upper and lower surfaces.*—Glossy.

*Venation pattern.*—Pinnate.

*Color.*—Developing leaves, upper surface: Between N186C and 187A. Developing leaves, lower surface: Close to N186C. Fully expanded leaves, upper surface: Close to 187A; venation, close to 187A. Fully expanded leaves, lower surface: Close to 146B heavily tinged with close to N187B; venation, close to 185A.

Flower description:

*Flower type and flowering habit.*—Small rotate flowers arranged in terminal compound cymes; flowers face upright to slightly outward; freely flowering habit with about 250 flowers developing per inflorescence.

*Fragrance.*—None detected.

*Natural flowering season.*—Plants flower continuously during August and September in The Netherlands; plants begin flowering about nine months after planting.

*Postproduction longevity.*—Flowers last about two weeks on the plant; flowers persistent.

*Flower buds.*—Height: About 4 mm. Diameter: About 2 mm. Shape: Elliptic. Color: Close to 185B; towards the base, close to 158D.

*Inflorescence height.*—About 10.8 cm.

*Inflorescence diameter.*—About 10.5 cm.

*Flower diameter.*—About 7 mm.

*Flower depth.*—About 4.5 mm.

*Petals.*—Quantity per flower: Typically five in a single whorl; petals fused at the base. Length: About 4.5 mm. Lobe width: About 1.5 mm. Shape: Ovate. Apex: Acute. Margin: Entire. Texture, upper and lower surfaces: Smooth, glabrous. Color: When opening, upper surface: Close to 69D. When opening, lower surface: Close to 185B; towards the base, close to 158D. Fully opened, upper surface: Close to 69D; midvein, close to 58D; color does not fade with development. When opening, lower surface: Close to 185B to 185C; towards the base, close to 69C to 69D.

*Sepals.*—Quantity per flower: Typically five in a single whorl, fused at the base; calyx, campanulate. Length: About 1.5 mm. Width: About 0.75 mm. Shape: Narrowly ovate. Apex: Acute. Margin: Entire. Texture, upper and lower surfaces: Smooth, glabrous. Color, when opening, upper and lower surfaces: Close to 187A. Color, fully opened, upper and lower surfaces: Close to 187A.

*Peduncles.*—Length: About 9.3 cm. Diameter: About 2.5 mm. Angle: Erect to about 45° from vertical. Strength: Moderately strong. Texture: Smooth, glabrous. Color: Close to 187B.

*Pedicels.*—Length: About 3 mm. Diameter: About 0.75 mm. Angle: Erect to about 50° from vertical. Strength: Moderately strong. Texture: Smooth, glabrous. Color: Close to 187B to 187C.

*Reproductive organs.*—Stamens: Quantity per flower: Typically ten. Filament length: About 1.5 mm. Filament color: Close to 150D. Anther shape: Broadly oblong, flattened. Anther length: About 0.5 mm. Anther color: Close to 3C. Pollen amount: Scarce. Pollen color: Close to 5B to 5C. Pistils: Quantity per flower: Typically five. Pistil length: About 0.7 mm. Stigma shape: Pointed. Stigma color: Close to 182D. Style length: About 0.5 mm. Style color: Close to 185C; color becoming closer to 185A with development. Ovary color: Close to 154C to 154D; color becoming closer to 184A and 187D with development.

*Seeds and fruits.*—Seed and fruit development have not been observed on plants of the new *Sedum*.

Disease & pest resistance: Plants of the new *Sedum* have not been noted to be resistant to pathogens and pests common to *Sedum* plants.

Garden performance: Plants of the new *Sedum* have been observed to have good garden performance and to tolerate rain, wind and high temperatures about 35° C. and to be winter hardy to USDA Hardiness Zone 5.

It is claimed:

1. A new and distinct *Sedum* plant named 'Chocolate Cherry' as illustrated and described.

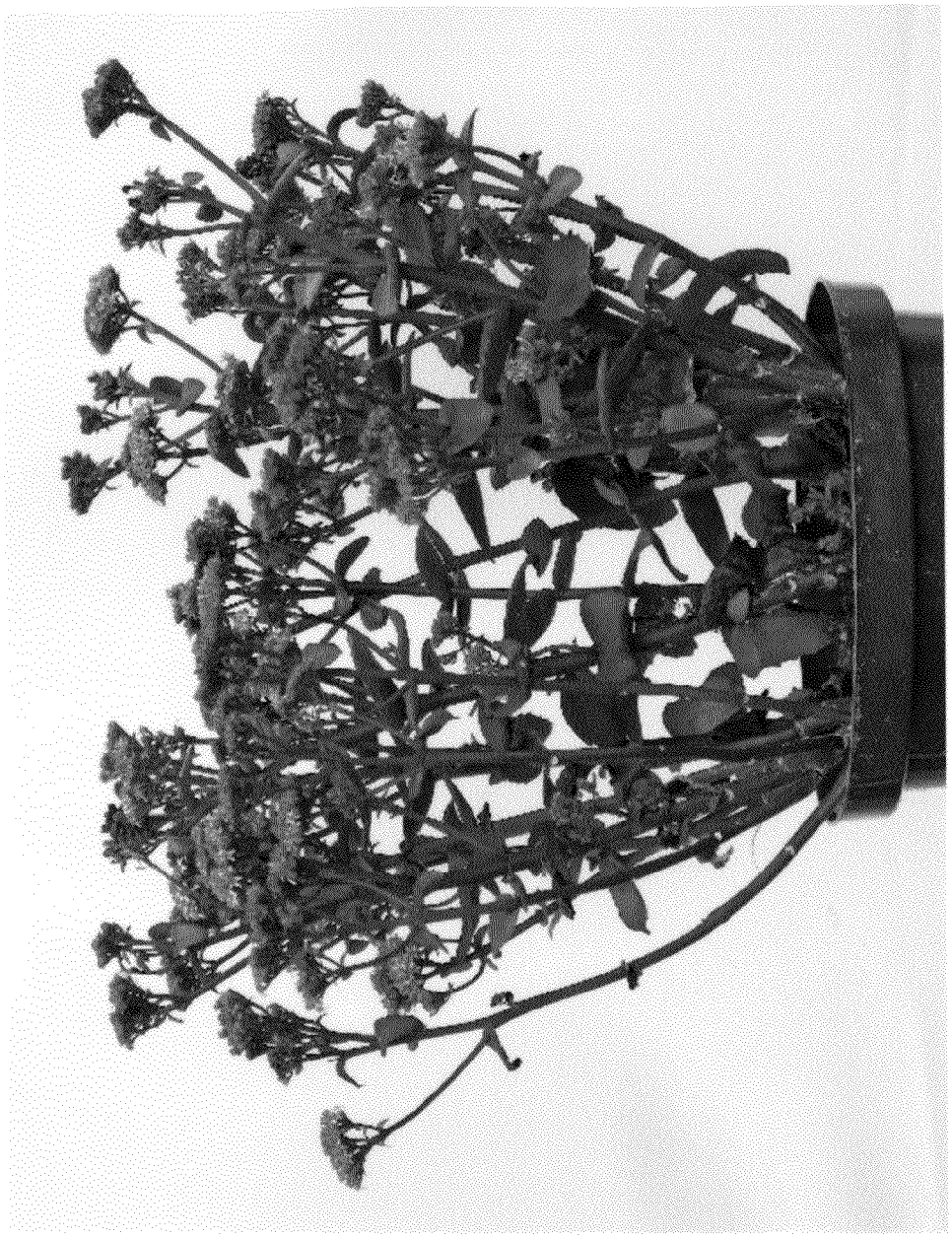

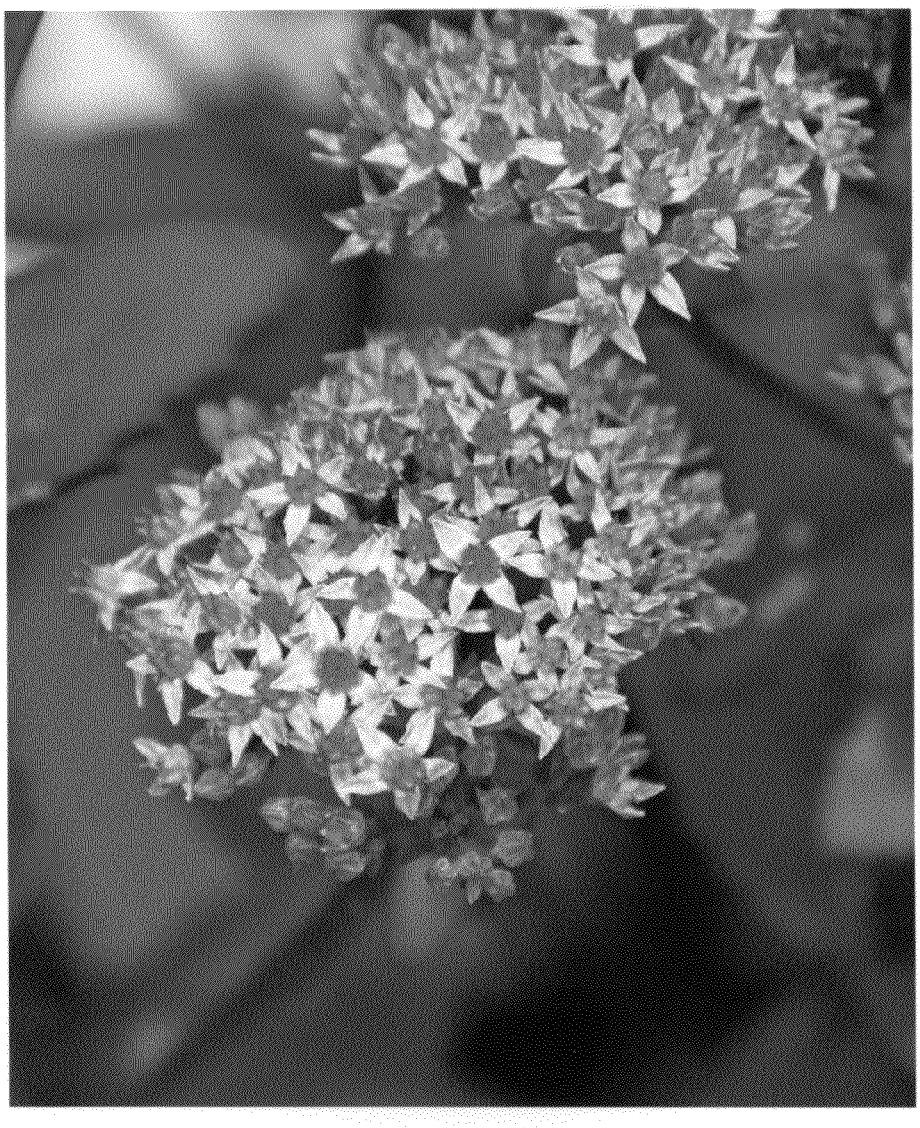

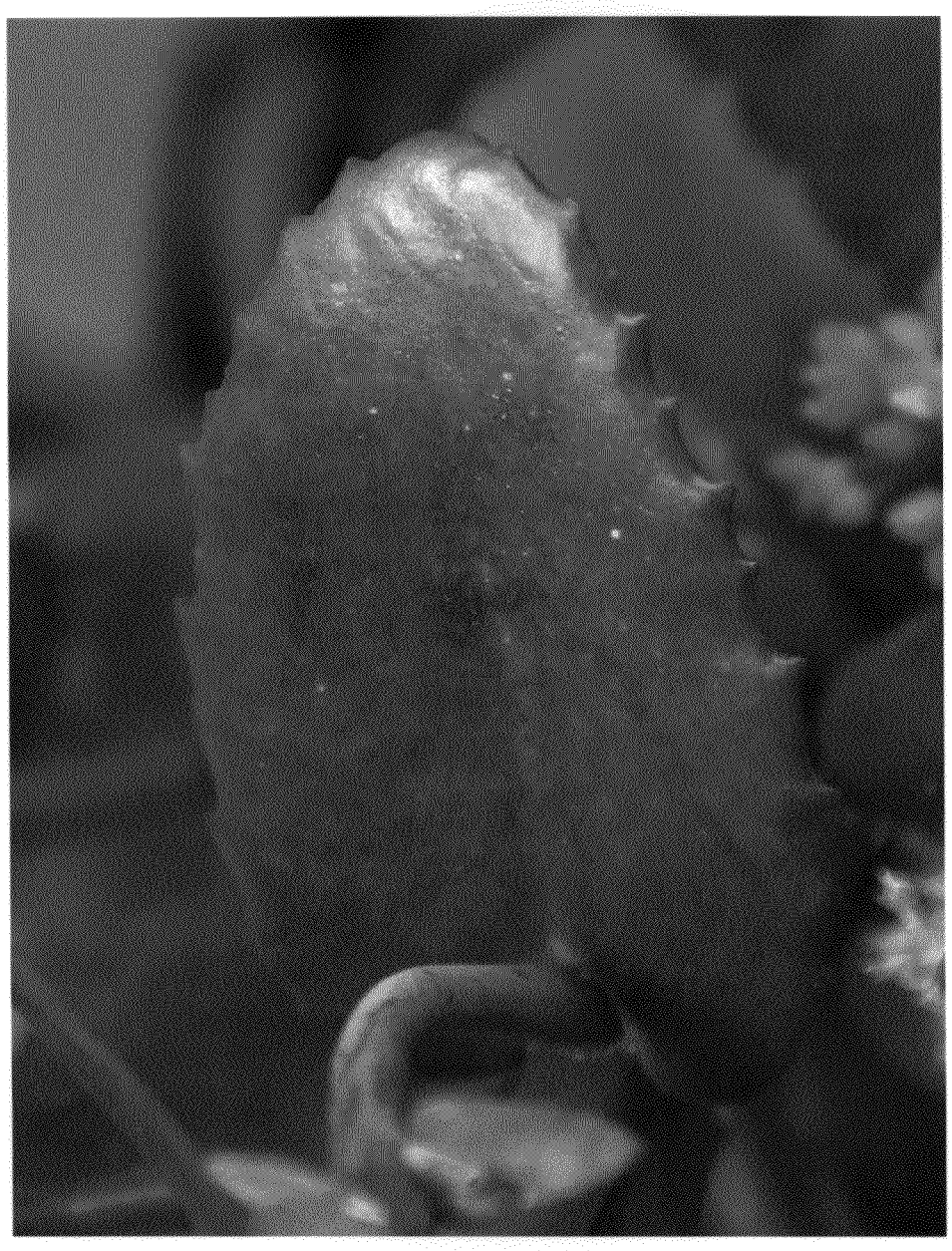

* * * * *